United States Patent
Herskovitz

(10) Patent No.: US 6,341,429 B1
(45) Date of Patent: Jan. 29, 2002

(54) SELF-EXAMINATION GRID

(75) Inventor: Stuart Herskovitz, Edgewood, NY (US)

(73) Assignee: Qosina Corp., Edgewood, NY (US)

( * ) Notice: Subject to any disclaimer, the term of this patent is extended or adjusted under 35 U.S.C. 154(b) by 0 days.

(21) Appl. No.: 09/451,895

(22) Filed: Dec. 1, 1999

(51) Int. Cl.$^7$ ................................................ A61B 5/103
(52) U.S. Cl. ......................... 33/512; 510/447; D28/8.1; 33/1 BB
(58) Field of Search ............................... 33/1 B, 1 BB, 33/1 F, 1 G, 121, 122, 511, 512, 563; 510/447, 449, 450; 600/300, 306, 587; D28/8.1

(56) References Cited

U.S. PATENT DOCUMENTS

| | | | | |
|---|---|---|---|---|
| 752,617 | A | * 2/1904 | DePue | .......................... 33/1 B |
| 1,495,978 | A | * 6/1924 | Anderson | .................... 510/449 |
| 1,707,334 | A | * 4/1929 | Unfried | ........................ 510/447 |
| 1,764,009 | A | * 6/1930 | Embree | ........................ 510/447 |
| 2,613,185 | A | * 10/1952 | Marshall | ...................... D28/8.1 |
| D192,131 | S | * 1/1962 | Weiss | .......................... D28/8.1 |
| 4,131,998 | A | * 1/1979 | Spears | ........................... 600/587 |
| 4,279,259 | A | 7/1981 | Lee et al. | |
| 4,389,782 | A | 6/1983 | Webster | |
| 4,483,075 | A | 11/1984 | Kundin | |
| 4,909,543 | A | * 3/1990 | Haskelson | ................... 283/117 |
| 4,965,008 | A | * 10/1990 | Chang | ......................... 510/449 |
| D318,244 | S | 7/1991 | Eichbaum | |
| 5,174,037 | A | 12/1992 | Curtin | |
| D337,483 | S | * 7/1993 | Newton | ........................ D7/409 |
| D341,223 | S | * 11/1993 | Sawyer | ......................... D28/8.1 |
| 5,265,605 | A | * 11/1993 | Afflerbach | ................... 600/300 |
| 5,285,785 | A | * 2/1994 | Meyer | .......................... 33/512 |
| D365,634 | S | * 12/1995 | Morgan | ...................... D24/155 |
| 5,507,740 | A | 4/1996 | O'Donnell, Jr. | |
| 5,657,753 | A | 8/1997 | Jacober et al. | |
| 5,741,212 | A | 4/1998 | Matthews | |
| D420,465 | S | * 2/2000 | Cascio | ......................... D28/8.1 |
| 6,174,845 | B1 | * 1/2001 | Rattinger et al. | ........... 510/447 |
| 6,219,930 | B1 | * 4/2001 | Reid | ............................ 33/121 |

* cited by examiner

Primary Examiner—G. Bradley Bennett
(74) Attorney, Agent, or Firm—Reed Smith LLP

(57) ABSTRACT

A bar of transparent soap contains a opaque rectilinear grid having square cells along a central plane of the bar of soap. In use, the soap applied to the skin of the user providing indication whether or not a skin abnormality such as a mole is growing.

9 Claims, 1 Drawing Sheet

SELF-EXAMINATION GRID

BACKGROUND OF THE INVENTION

This invention relates in general to a device to facilitate and encourage sufficiently quantitative examination of one's own skin so as to provide useful information concerning the growth of skin abnormalities such as moles.

There are a number of known techniques for providing a grid which can be used to examine and estimate the growth of various skin abnormalities. These grids are generally incorporated in a clear plastic sheet that can be placed against the skin of the individual to provide comparative measurements of the growth of an abnormality over a period of time. These prior art devices are generally employed by heath care practitioners on patients although there is nothing inherent in them that would prevent the patient from using them on themselves. But the context is one that fails to provide the ease of convenient use that would encourage daily use. Daily use increases the assurance that an active growth would be fairly promptly identified. One such prior art devices is shown in U.S. Pat. No. 4,389,782 issued on Jan. 28, 1983.

Accordingly, the major purpose of this invention is to provide a self-examination grid situated in a media which will encourage if not assure daily use.

BRIEF DESCRIPTION

In brief, the preferred embodiment of this invention involves a bar of essentially transparent soap having a centrally placed opaque grid in a plane that is parallel to the two major surfaces of the bar of soap. The grid is preferably a square grid have orthogonal lines equally spaced apart in both directions.

By placing the lines of the embedded grid essentially in the center plane of the bar of soap, it will be visible and available to the user throughout almost the entire usable life of the soap bar.

The presence of the bar in the soap bar tends to assure daily access to the grid and tends to assure proximity of the grid to the user's skin so as to facilitate and encourage daily use.

DESCRIPTION OF THE PREFERRED EMBODIMENTS

Figure 1:
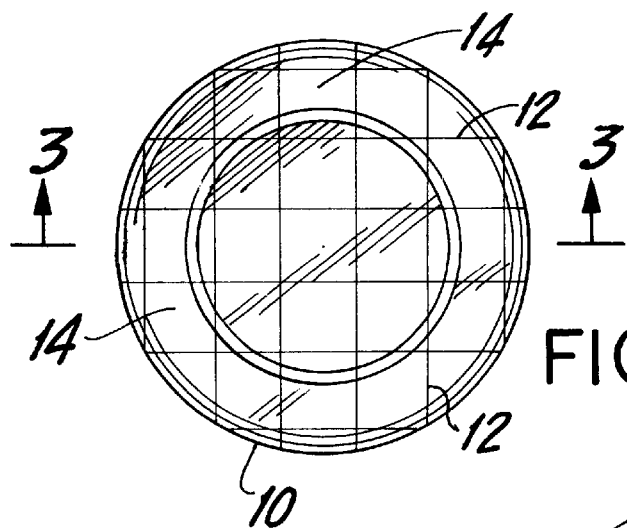
FIG. 1 is a plan view of the device of the invention showing the grid embedded in a bar of soap.
Figure 2:
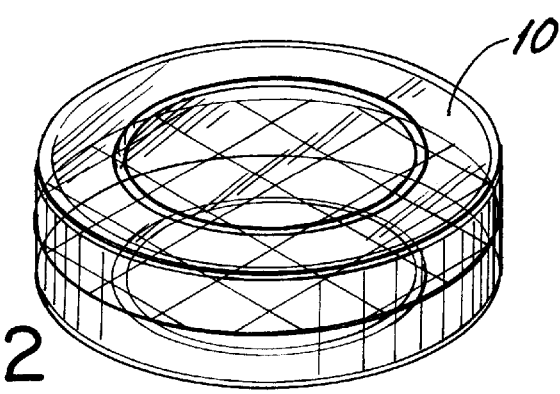
FIG. 2 is a perspective view of the FIG. 1 embodiment.
Figure 3:
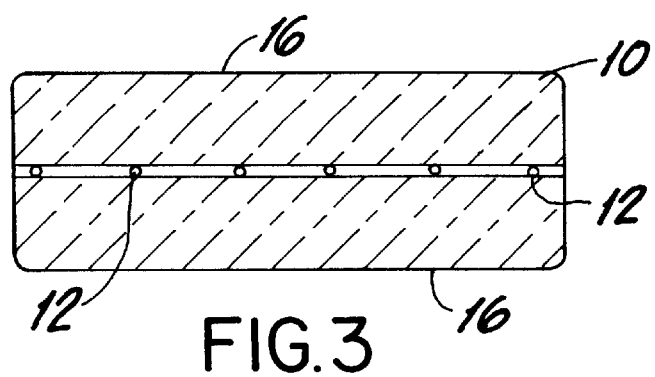
FIG. 3 is a cross-sectional view along the plane 3—3 of the FIG. 1 embodiment.

With reference to the FIGS, which all illustrate a single embodiment, there is shown a bar of soap 10 in which is embedded, on a central plane, an opaque grid 12. The grid 12 is arranged in a rectilinear format having intersecting lines which are orthogonal to one another. The parallel grid lines are spaced apart at equal distances from one another so that each cell 14 defined by the grid lines is a square. In one embodiment, the distance between adjacent parallel grid lines is one centimeter.

The soap 10 itself is substantially clear or transparent so that the grid 12 will be readily visible. The grid lines are opaque lines which can be formed from a soap material. Alternately, the grid can be laid in as a grid of some separate material. It is believed that if the grid lines are made of a soap material, such would enhance the willingness of the user to continue to use replacement soaps as each is used up and thus further encourage the continuing daily use of this device to enable self-detection of skin abnormalities.

The soap bar 10 has two parallel main surfaces 16. The grid 12 is deployed in a center zone parallel to the two faces. The grid is preferably in the middle but could be useful if deployed anywhere between one-third to two-thirds of the way from one of the main surfaces 16.

Figure 4:
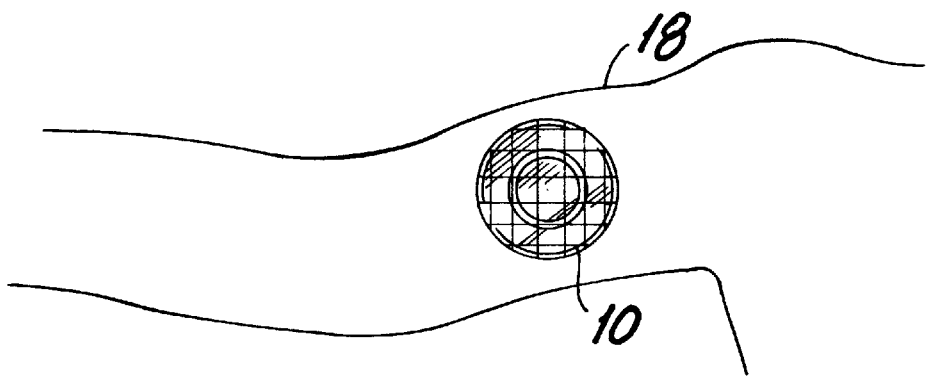
FIG. 4 shows the FIG. 1 embodiment of this invention positioned on the arm of a user.

As shown in FIG. 4, the soap bar 10 is laid on the skin 18 of the user with whatever skin abnormality or lesion that is of concern centered on one of the cells 14 so that growth of the item of concern can be determined.

One specific technique found to work to lay down the grid 12 in the center zone of the soap bar is the following:

When the soap is being molded, and the mold is half filed, an ink-jet printer is used to print the grid 12 directly onto the half bar. The mold is then filed with the rest of the half bar and the resulting product 10 is obtained.

Alternatively, a pre-printed clear dissolvable layer such as a rice paper layer with the grid 12 printed thereon can be laid into the mold when the mold is half filed with soap to thereby form the grid.

The important point about using the soap bar as a media for carrying the grid is that the user will tend to be using the soap bar on a daily basis and will be applying it to the user's skin. Accordingly, the user can readily, without taking any special steps, examine skin abnormalities to determine if there is a growth change. After all, there is a tendency to put off these checks and, in some individuals, some denial which causes resistence to taking special steps to making these examinations. If the examination step is almost automatic, the user has less resistant or "excuse" to avoid the examinations. Thus there is greater likelihood of making the examination.

It is believed that other daily use bathroom implements might be a media on which this grid could be laid down to facilitate regular daily use. Although not as nearly automatic as the bar of soap embodiment described above, it is contemplated that it could be embedded in items such as a transparent handle of a hairbrush or other device which is used on a regular basis in the bathroom by a user.

There might even be circumstances in which a relatively small grid having relatively few cells could be deployed in the transparent handle of a toothbrush. The daily personal use of a toothbrush would encourage applying the handle with a grid on it to the skin abnormality.

What I claim is:

1. A measuring device comprising:
    a transparent bar of soap, and
    a predetermined grid having at least one square cell embedded in said transparent bar of soap,
    said cell being of a size adapted to facilitate obtaining an indication of the extent of growth of a skin abnormality.
2. The measuring device of claim 1 wherein said grid is deployed in the center zone of said bar of soap.
3. The measuring device of claim 1 wherein said grid has a plurality of square cells.
4. The measuring device of claim 2 wherein said grid has a plurality of square cells.
5. The measuring device of claim 1 wherein said bar of soap has first and second main surfaces, and said grid is substantially parallel to said first and second main surfaces.
6. The measuring device of claim 5 wherein said center zone is between one-third and two-thirds of the distance from one of said main surfaces.
7. The measuring device of claim 5 wherein said grid has a plurality of square cells.
8. The measuring device of claim 6 wherein said grid has a plurality of square cells.
9. The measuring device of claim 8 wherein said grid is formed from an opaque soluble material.

* * * * *